United States Patent
El Dib et al.

(10) Patent No.: US 10,947,265 B2
(45) Date of Patent: Mar. 16, 2021

(54) SYNTHESIS OF URSOLIC ACID NANOPARTICLES

(71) Applicant: KING SAUD UNIVERSITY, Riyadh (SA)

(72) Inventors: Rabab Abd El Moneim Khalil El Dib, Giza (EG); Shaza Mohamed Adel Al-Massarani, Riyadh (SA); Manal Ahmed Gasmelseed Awad, Riyadh (SA); Ali Ali Hasan Elgamal, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 16 days.

(21) Appl. No.: 16/552,496

(22) Filed: Aug. 27, 2019

(65) Prior Publication Data

US 2020/0165293 A1 May 28, 2020

Related U.S. Application Data

(62) Division of application No. 16/202,046, filed on Nov. 27, 2018.

(51) Int. Cl.
| | |
|---|---|
| *A61K 36/00* | (2006.01) |
| *C07J 63/00* | (2006.01) |
| *A01N 65/00* | (2009.01) |
| *B82Y 40/00* | (2011.01) |

(52) U.S. Cl.
CPC ............ *C07J 63/008* (2013.01); *A01N 65/00* (2013.01); *B82Y 40/00* (2013.01)

(58) Field of Classification Search
None
See application file for complete search history.

(56) References Cited

U.S. PATENT DOCUMENTS 10,307,450 B2 * 6/2019 Addington ............. A61K 36/24
2009/0028969 A1   1/2009 Sene et al.

FOREIGN PATENT DOCUMENTS

RU       2494754 C1   10/2013

OTHER PUBLICATIONS

Zhou et al. (2009) Drug Development and Industrial Pharmacy, 35:3: 305-310. (Year: 2009).*
Massarani et al. "New Cytotoxic Seco-Type Triterpene and Labdane-Type Dipertenes from Nuxia oppositifolia", Molecules (Mar. 2017), 22(3), 389 (11 pages).
Yang et al., "Physicochemical properties and oral bioavailability of ursolic acid nanoparticles using supercritical anti-solvent (SAS) process", Food Chemistry (2012), vol. 132, Iss. 1, pp. 319-325 (Abstract only).
Zhang et al., "Delivery of ursolic acid (UA) in polymeric nanoparticles effectively promotes the apoptosis of gastric cancer cells through enhanced inhibition of cyclooxygenase 2 (COX-2)", International Journal of Pharmaceutics (2013), vol. 441, Iss. 1-2, pp. 261-268 (Abstract only).
Ge et al., "Enhanced oral bioavailability of ursolic acidnanoparticles via antisolvent precipitation with TPGS1000 as a stabilizer", Journal of Drug Delivery Science and Technology (2015). vol. 29, pp. 210-217 (Abstract only).
Jin et al., "Folate-Chitosan Nanoparticles Loaded with Ursolic Acid Confer Anti-Breast Cancer Activities in vitro and in vivo", Scientific Reports (2016), 6:30782, 11 pages.
Valdes et al., "Potential use of nanocarriers with pentacyclic triterpenes in cancer treatments", Nanomedicine (2016), vol. 11, No. 23 (Abstract only).
Liu et al., "Self-assembled nanoparticles based on carboxymethyl cellulose-ursolic acid conjugate for anticancer combination therapy", RSC Adv. (2017), vol. 7, pp. 36256-36268.
Wang et al., "Ursolic acid nanoparticles inhibit cervical cancer growth in vitro and in vivo via apoptosis induction", Int.. Oncol. (2017) 50(4), pp. 1330-1340 (Abstract only).

\* cited by examiner

*Primary Examiner* — Russell G Fiebig
(74) *Attorney, Agent, or Firm* — Nath, Goldberg & Meyer; Richard C. Litman

(57) ABSTRACT

The synthesis of ursolic acid nanoparticles includes dissolving ursolic acid powder in methanol, boiling water for five minutes, and adding the methanol solution to the boiled water dropwise at a flow rate of 0.1-0.3 ml/min under ultrasonic conditions. After sonication for 20 minutes, the contents are stirred for about 15 minutes, and then dried. Particle size distribution studies and TEM micrographs confirm the resulting product comprises nanoparticles. In vitro testing confirms the ursolic acid nanoparticles exhibit greater anticancer activity than conventional-size particles, and that the nanoparticles exhibit antimicrobial effect against gram positive and gram negative bacteria, as well as fungi.

1 Claim, 8 Drawing Sheets

SYNTHESIS OF URSOLIC ACID NANOPARTICLES

BACKGROUND

1. Field

The disclosure of the present patent application relates to triterpenes having potential use in medicine, and particularly to a synthesis of ursolic acid nanoparticles.

2. Description of the Related Art

Ursolic acid is a pentacyclic triterpenoid found in many fruits and herbs. Various in vitro studies have shown that ursolic acid exhibits anticancer activity, and also displays anti-inflammatory and immune system modulation activities. However, it is believed unlikely that ursolic acid would have any direct clinical application exactly as it is found in nature, since, like many pentacyclic triterpenoids, ursolic acid is hydrophobic, and it would therefore be difficult to deliver as an active ingredient to tissues in need of treatment without modification. Consequently, there has been a good deal of interest in recent years in developing ursolic acid nanoparticles and nano-based drug delivery systems for ursolic acid. Thus, a synthesis of ursolic acid nanoparticles solving the aforementioned problems is desired.

SUMMARY

The synthesis of ursolic acid nanoparticles includes dissolving ursolic acid powder in methanol, boiling water for five minutes, and adding the methanol solution to the boiled water dropwise at a flow rate of 0.1-0.3 ml/min under ultrasonic conditions. After sonication for 20 minutes, the contents are stirred for about 15 minutes, and then dried. Particle size distribution studies and TEM micrographs confirm the resulting product comprises nanoparticles. In vitro testing confirms the ursolic acid nanoparticles exhibit greater anticancer activity than conventional-size particles, and that the nanoparticles exhibit antimicrobial effect against gram positive and gram negative bacteria, as well as fungi.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The compound ursolic acid was obtained from the n-hexane fraction of the aerial parts of the Saudi plant *Nuxia oppositifolia*, following the application of a number of chromatographic purification techniques. The structure was assigned by different spectroscopic methods, including IR and 1 and 2-D NMR and comparison with published data. Ursolic acid is a pentacyclic triterpenoid widely found in the peels of fruits such as apple and prunes, as well as in herbs and spices, such as rosemary and thyme. Ursolic acid has been reported to inhibit the proliferation of different cancer cell types by inhibiting the STAT3 activation pathway. Ursolic acid has the following structure:

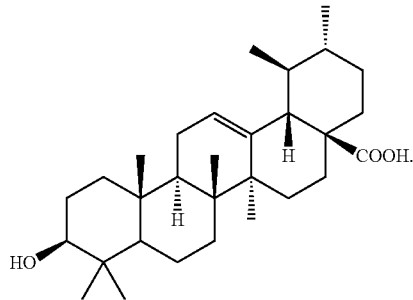

The synthesis of ursolic acid nanoparticles includes dissolving ursolic acid powder in methanol, boiling water for five minutes, and adding the methanol solution to the boiled water dropwise at a flow rate of 0.1-0.3 ml/min under ultrasonic conditions. After sonication for 20 minutes, the contents are stirred for about 15 minutes, and then dried. Particle size distribution studies and TEM micrographs confirm the resulting product comprises nanoparticles. In vitro testing confirms the ursolic acid nanoparticles exhibit greater anticancer activity than conventional-size particles, and that the nanoparticles exhibit antimicrobial effect against gram positive and gram negative bacteria, as well as fungi.

The synthesis of ursolic acid will be better understood by reference to the following examples.

Example 1

Extraction of Ursolic Acid

The dried and powdered aerial parts of *N. oppositifolia* (900 g) were extracted by maceration with 80% ethanol (4×2

L) at room temperature. The combined ethanol extract was filtered and concentrated under reduced pressure at 40° C. using a rotary evaporator. The dried ethanol extract (105 g) was redissolved in 40% ethanol and successively partitioned several times with n-hexane (3×500 mL) and n-butanol (3×500 mL) to provide the corresponding extracts. The n-hexane fraction (17.6 g) was subjected to column chromatography on pre-packed silica gel column (40 mm i.d× 350 mm) and eluted with n-hexane-ethyl acetate gradient. The collected fractions were examined with thin layer chromatography (TLC), and similar ones were pooled together into four fractions (A-D). Fraction C eluted with 20% EtOAc/n-hexane, afforded ursolic acid after solvent evaporation. It will be understood that the foregoing extraction of ursolic acid from *N. oppositifolia* is representative of one manner of obtaining ursolic acid powder, and that ursolic acid obtained from any other source or by any other method may be used for the synthesis of ursolic acid nanoparticles as described herein.

Example 2

Characterization of Ursolic Acid

Figure 1:
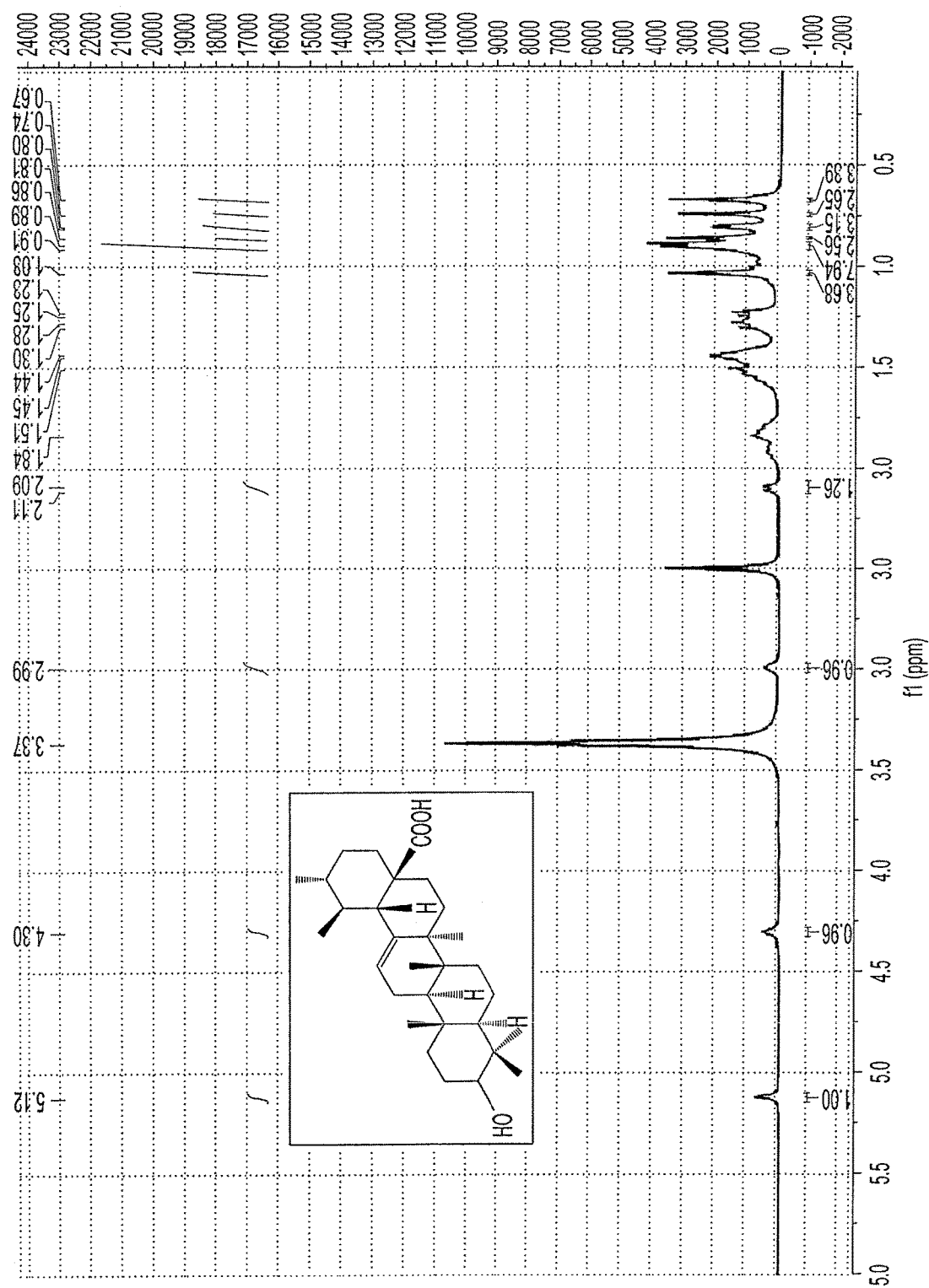
FIG. 1 is the $^1$H NMR spectrum of the synthesized ursolic acid nanoparticles.
Figure 2:
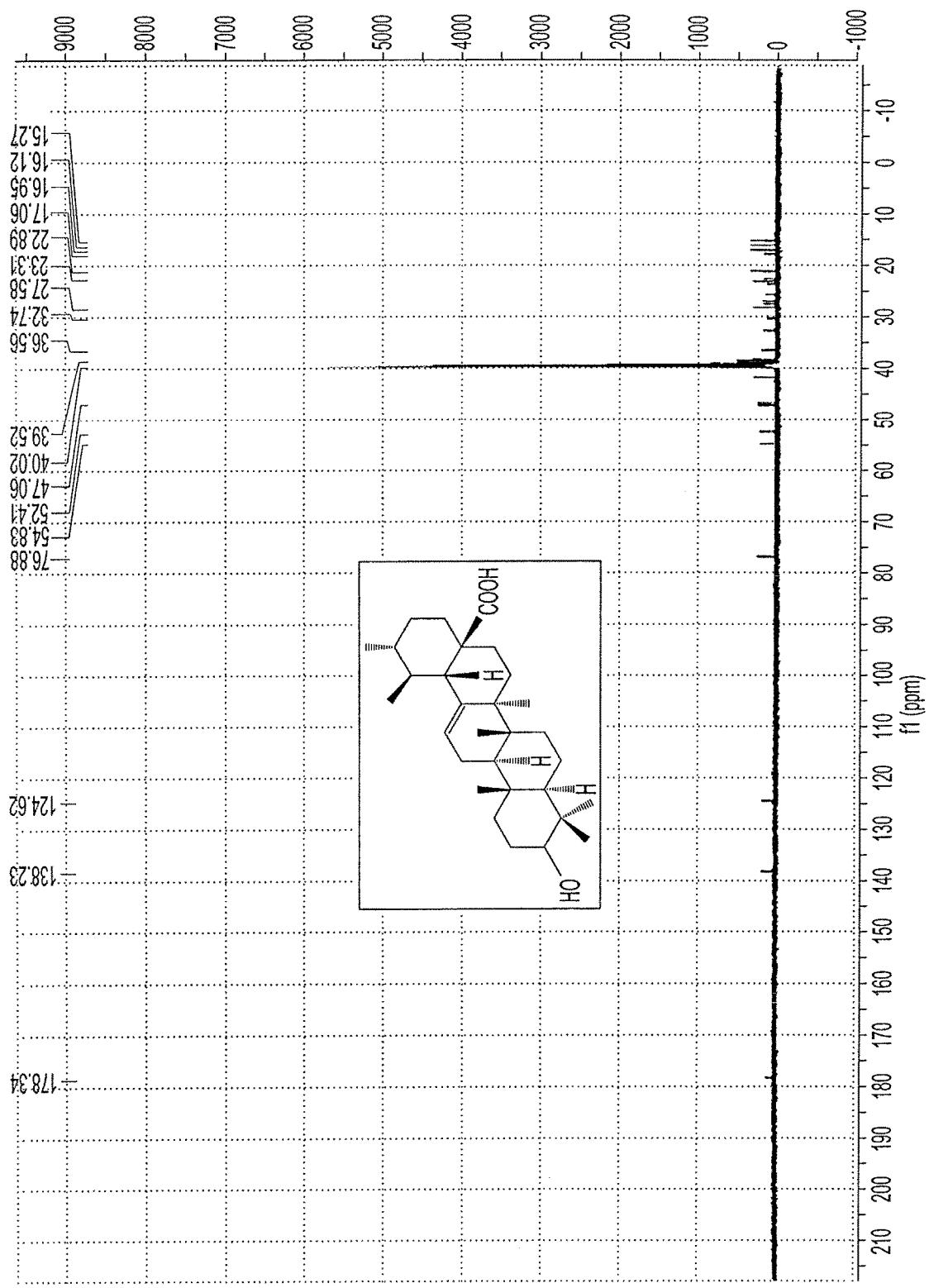
FIG. 2 is the complete $^{13}$C NMR spectrum of the synthesized ursolic acid nanoparticles.
Figure 3:
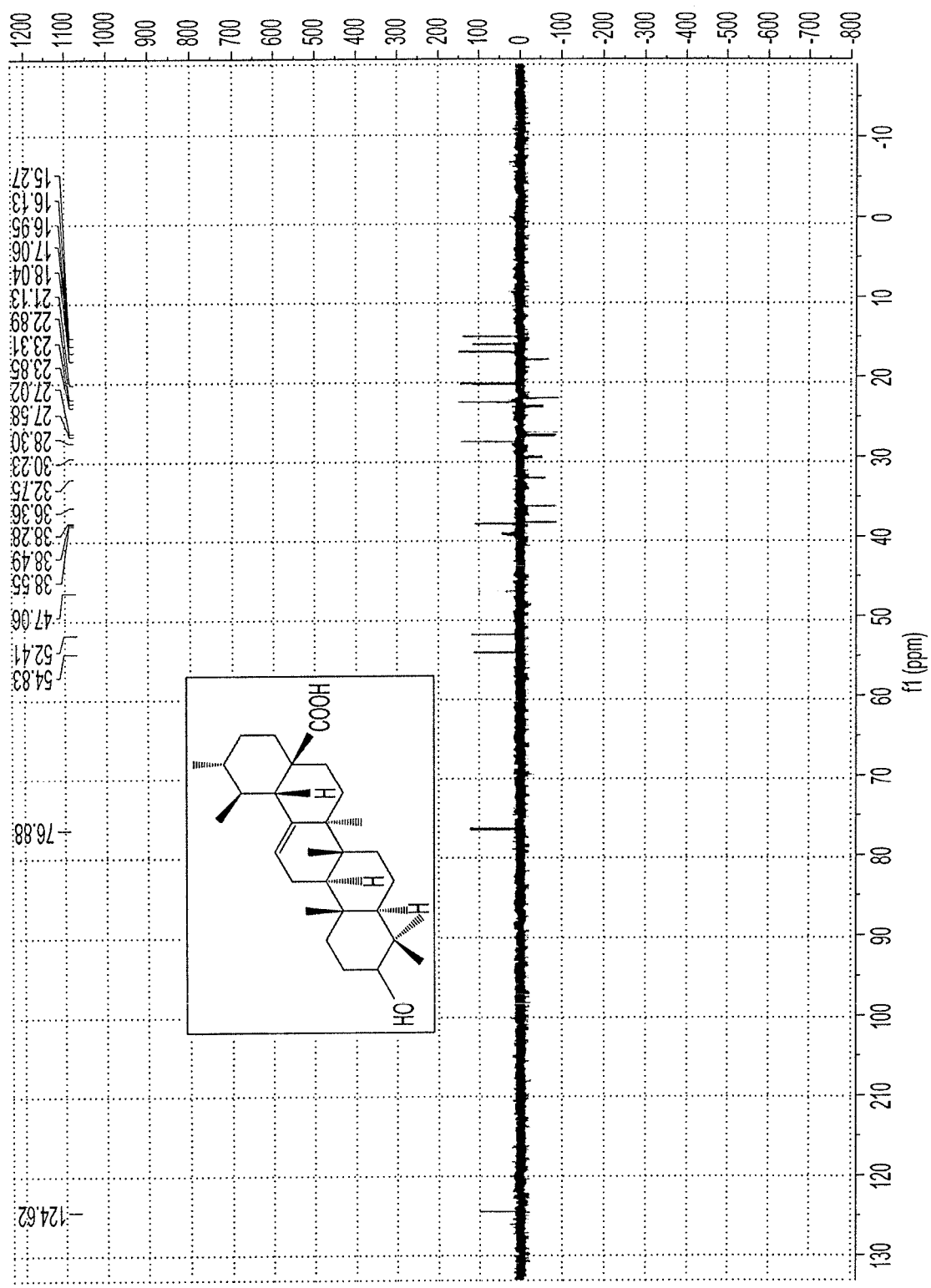
FIG. 3 is the DEPT $^{13}$C NMR spectrum of the synthesized ursolic acid nanoparticles.

Ursolic acid, synthesized as described in Example 1, was characterized by $^1$H NMR (shown in FIG. 1) and $^{13}$C NMR (shown in FIGS. 2 and 3. The NMR spectra confirmed that the substance obtained by extraction of *N. oppositifolia* is indeed ursolic acid, as shown by comparison to NMR spectra of known samples of ursolic acid.

Example 3

Synthesis of Ursolic Acid Nanoparticles

The powder of ursolic acid (50 mg) was dissolved in 10 ml methanol (solution A). Water (40 mL) was boiled, and then 5 ml of solution A was added dropwise to the boiled water with a flow rate of 0.1-0.3 ml/min in 10 minutes under ultrasonic conditions. After sonication for 20 min, the contents were stirred for about 15 minutes then dried.

Example 4

Characterization of Ursolic Acid Nanoparticles

Figure 4:
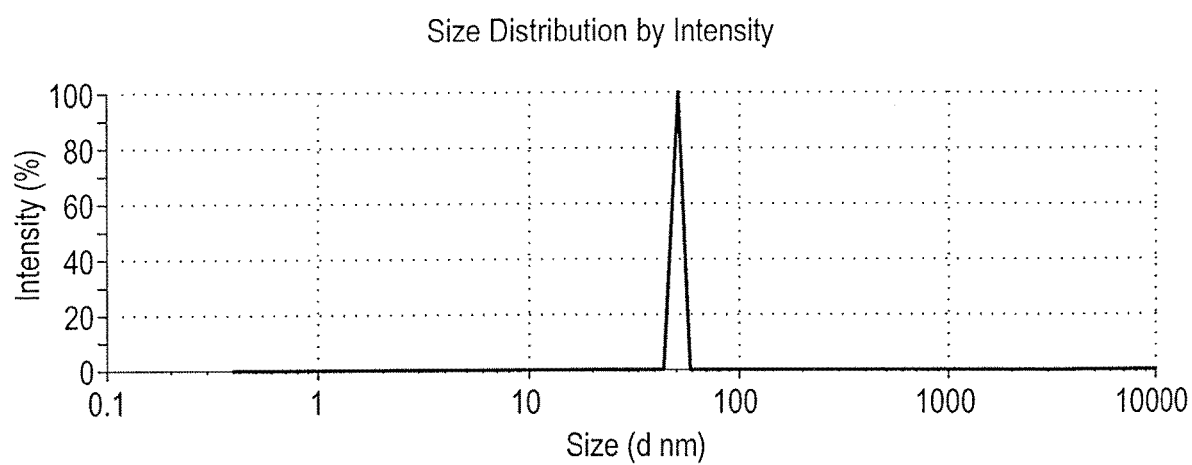
FIG. 4 is a Zetasizer particle size distribution curve of the synthesized ursolic acid nanoparticles.
Figure 5A:
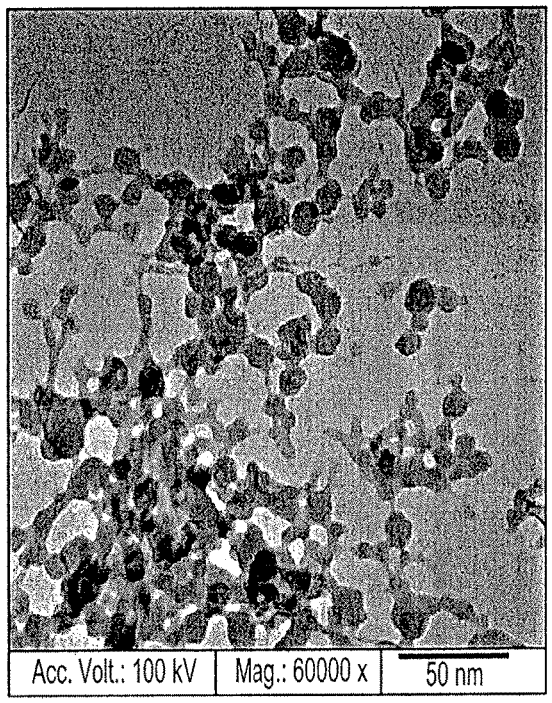
FIGS. 5A, 5B, and 5C are TEM micrographs of the synthesized ursolic acid nanoparticles at a magnification of 60000×.
Figure 5B:
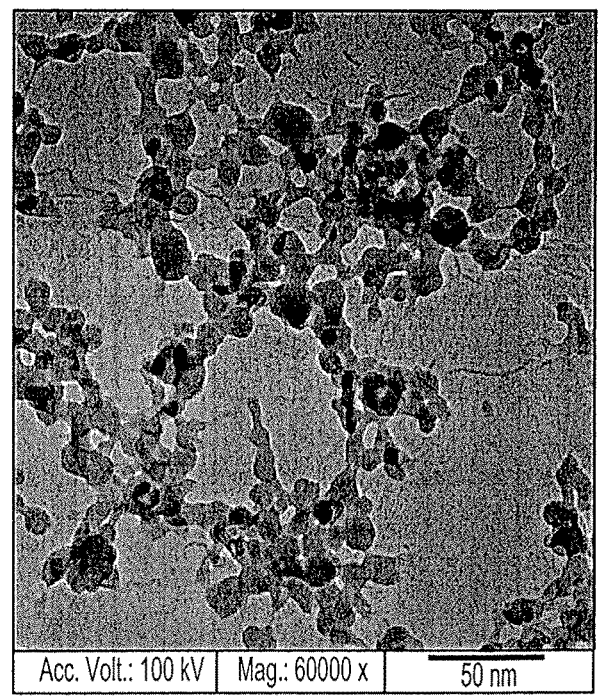
Figure 5C:
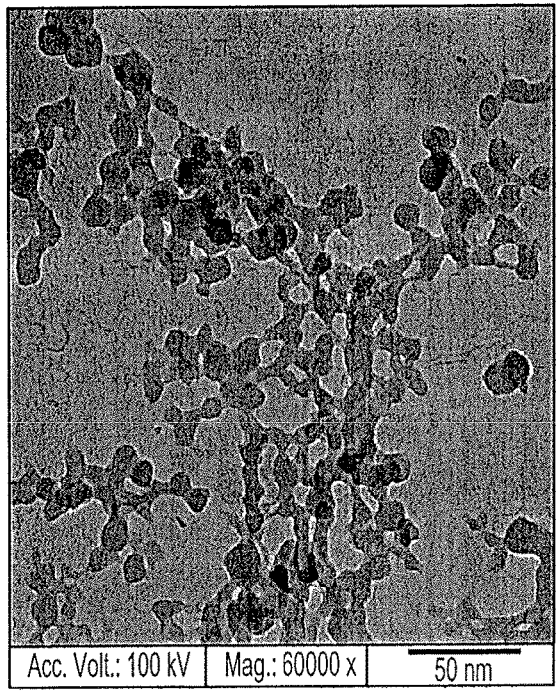
Figure 5D:
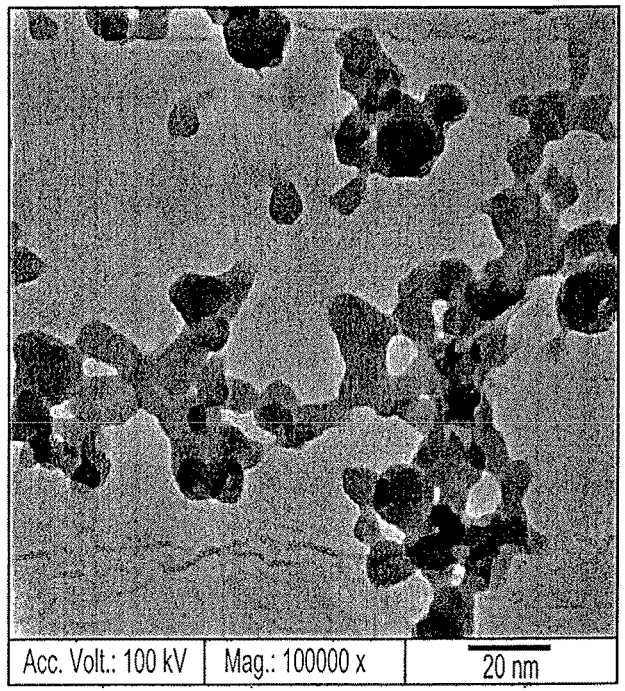
FIG. 5D is a TEM micrograph of the synthesized ursolic acid nanoparticles at a magnification of 100000×.

The synthesized nanoparticles were characterized using Zetasizer, Nano series, HT Laser, ZEN3600 from Molvern Instrument, UK to determine the average size of the resulting nanoparticles. FIG. 4 shows a Zetasizer particle size distribution curve of the synthesized ursolic acid nanoparticles. It will be noted that the particle sizes fell within the range of 10-100 nm. Transmission electron microscopy (TEM, JEM-1400, JEOL, Japan) was also employed to characterize the size, shape and morphologies of nanoparticles. FIGS. 5A-5C are micrographs having a magnification of 60000×, and FIG. 5D is a micrograph having a magnification of 100000×. The particle sizes are in the range of 10-100 nm, and the particles are almost spherical, collected into necklace-shaped or network-like structures.

Example 5

Cytotoxicity Testing

Dimethyl sulfoxide (DMSO), crystal violet and trypan blue dye were purchased from Sigma (St. Louis, Mo., USA). Fetal Bovine serum, DMEM, RPMI-1640, HEPES buffer solution, L-glutamine, gentamycin and 0.25% Trypsin-EDTA were purchased from (Bio Whittaker® Lonza, Belgium).

Crystal violet, composed of 0.5% (w/v) crystal violet and 50% methanol, was used as staining solution. The mammalian cell lines used were obtained from the American Type Culture Collection (ATCC). The cells were propagated in Dulbeccos modified Eagles Medium (DMEM), supplemented with 10% heat-inactivated fetal bovine serum, 1% L-glutamine, HEPES buffer and 50 µg/mL gentamicin. Cells were maintained at 37° C. in a humidified atmosphere with 5% $CO_2$ and were sub-cultured two times a week.

The cytotoxic activity was evaluated by the crystal violet staining (CVS) method (Itagaki et al., 1991; Saotome et al., 1989). Briefly, the cells were seeded in a 96-well tissue culture microplate, at a concentration of 1×10⁴ cells per well in 100 µL of growth medium at 37° C. After 24 h of seeding, fresh medium containing various concentrations of the tested compounds (50, 25, 12.5, 6.25, 3.125 & 1.56 µg) were added to the microtiter plates (each compound was tested in triplicate in all concentrations). Next, the microtiter plates were incubated at 37° C. in a humidified incubator with 5% $CO_2$. Control cells were incubated without test sample and with or without DMSO. The little percentage of DMSO present in the wells was found not to affect the experiment. After 48 h incubation period, viable cells yield was determined by a colorimetric method. In brief, media were aspirated for 30 min and the crystal violet solution (1%) was added to each well. The plates were rinsed after removing the stain by distilled water. Glacial acetic acid (30%) was then added to all wells and mixed thoroughly. The quantitative analysis, to evaluate the fixed cells, was performed calorimetrically by measuring the absorbance in an automatic Microplate reader (TECAN, Inc.) at 595 nm. The effect on cell growth was calculated as the difference in absorbance percentage in the presence and absence of the tested compounds. A dose-response curve was plotted to acquire the concentration at which the growth of cells was inhibited to 50% of the control ($IC_{50}$). The standard antitumor drug used was doxorubicin.

Example 6

Cytotoxic Testing of MCF-7 Cell Line (Breast Carcinoma)

Figure 6:
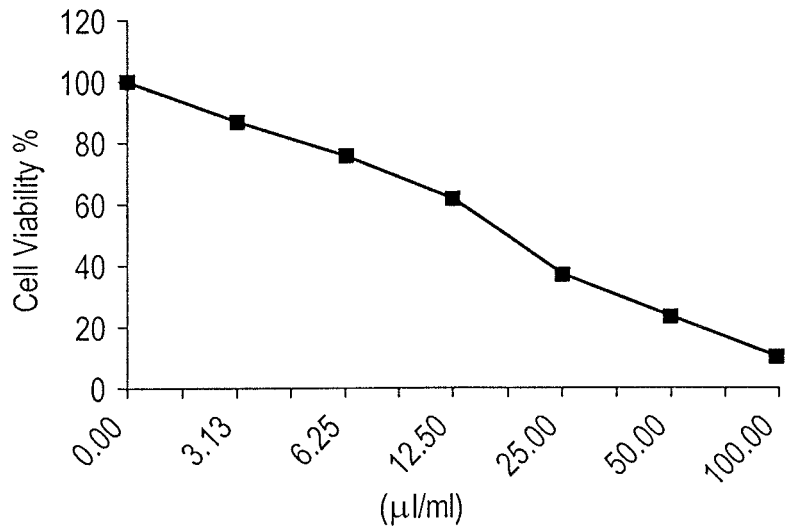
FIG. 6 is a plot of the cell viability (%) of the MCF-7 cell line as a function of the concentration (μl/ml) of synthesized ursolic acid nanoparticles.

The cytotoxic activity of the ursolic acid nanoparticles against the MCF-7 cell line (Breast carcinoma) was tested as described in the procedure of Example 5. The results are shown graphically in FIG. 6. The data shown graphically in FIG. 6 are summarized in Table 1 as follows.

TABLE 1

Inhibitory activity of ursolic acid nanoparticles against MCF-7 cells, $IC_{50}$ = 18.5

| Sample conc. (µl/ml) | % Viability (3 Replications) | | | | % Inhibition | Standard Deviation (±) |
|---|---|---|---|---|---|---|
| | 1st | 2nd | 3rd | Mean | | |
| 100 | 9.68 | 11.24 | 10.82 | 10.58 | 89.42 | 0.81 |
| 50 | 21.76 | 24.93 | 23.89 | 23.53 | 76.47 | 1.62 |
| 25 | 36.92 | 40.54 | 34.17 | 37.21 | 62.79 | 3.19 |
| 12.5 | 67.24 | 59.62 | 58.35 | 61.74 | 38.26 | 4.81 |
| 6.25 | 79.38 | 74.16 | 73.84 | 75.79 | 24.21 | 3.11 |
| 3.125 | 86.12 | 85.27 | 89.21 | 86.87 | 13.13 | 2.07 |

Example 7

Cytotoxic Testing of HepG-2 Cell Line (Hepatocellular Carcinoma)

Figure 7:
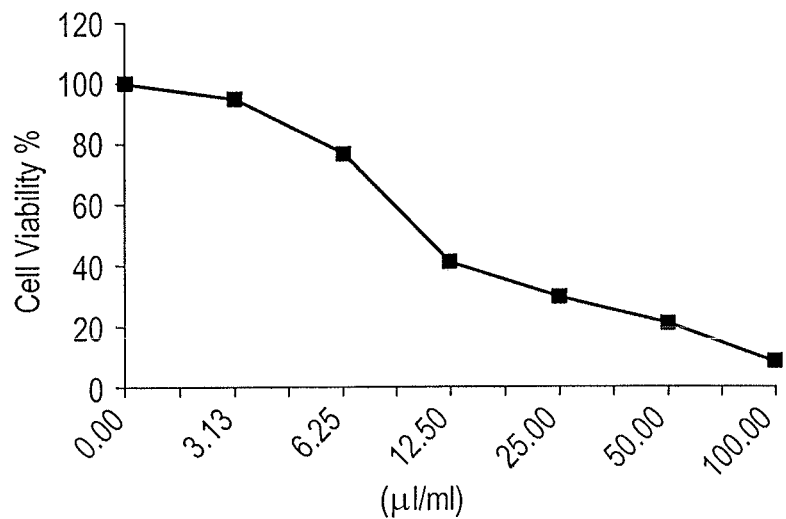
FIG. 7 is a plot of the cell viability (%) of the HepG-2 cell line as a function of the concentration (μl/ml) of synthesized ursolic acid nanoparticles.

The cytotoxic activity of the ursolic acid nanoparticles against the HepG-2 cell line (Liver carcinoma) was tested as described in the procedure of Example 5. The results are shown graphically in FIG. 7. The data shown graphically in FIG. 7 are summarized in Table 2 as follows.

TABLE 2

Inhibitory activity of ursolic acid nanoparticles against HEPG-2 cells, $IC_{50} = 10.9$

| Sample conc. (µl/ml) | % Viability (3 Replications) | | | | % Inhibition | Standard Deviation (±) |
|---|---|---|---|---|---|---|
| | 1st | 2nd | 3rd | Mean | | |
| 100 | 7.65 | 8.14 | 9.86 | 8.55 | 91.45 | 1.16 |
| 50 | 23.97 | 20.32 | 19.41 | 21.23 | 78.77 | 2.41 |
| 25 | 31.64 | 29.06 | 27.93 | 29.54 | 70.46 | 1.90 |
| 12.5 | 43.98 | 40.87 | 38.54 | 41.13 | 58.87 | 2.73 |
| 6.25 | 76.42 | 79.51 | 74.29 | 76.74 | 23.26 | 2.62 |
| 3.125 | 94.27 | 96.34 | 93.82 | 94.81 | 5.19 | 1.34 |

Example 8

Cytotoxic Testing of HCT-116 Cell Line (Colon Carcinoma)

Figure 8:
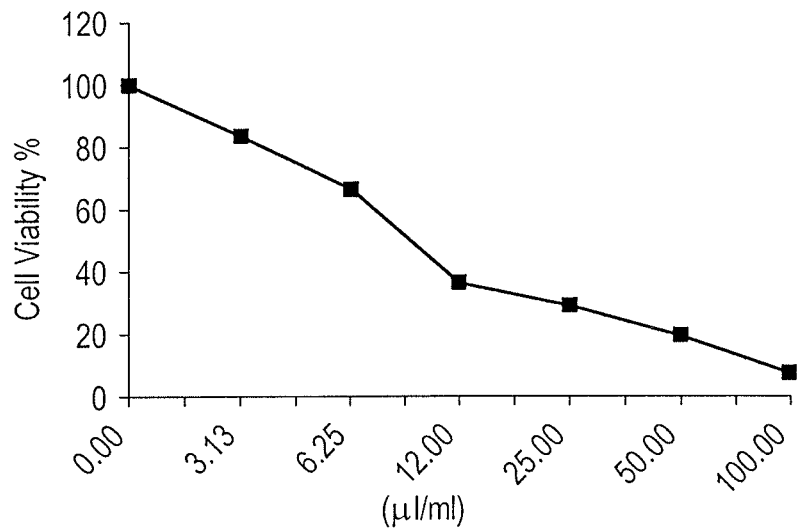
FIG. 8 is a plot of the cell viability (%) of the HCT-116 cell line as a function of the concentration (μl/ml) of synthesized ursolic acid nanoparticles.

The cytotoxic activity of the ursolic acid nanoparticles against the HCT-116 cell line (Human colon carcinoma) was tested as described in the procedure of Example 5. The results are shown graphically in FIG. 8. The data shown graphically in FIG. 8 are summarized in Table 3 as follows.

TABLE 3

Inhibitory activity of ursolic acid nanoparticles against HCT-116 cells, $IC_{50} = 9.7$

| Sample conc. (µl/ml) | % Viability (3 Replications) | | | | % Inhibition | Standard Deviation (±) |
|---|---|---|---|---|---|---|
| | 1st | 2nd | 3rd | Mean | | |
| 100 | 8.16 | 7.34 | 7.98 | 7.83 | 92.17 | 0.43 |
| 50 | 21.84 | 19.47 | 18.29 | 19.87 | 80.13 | 1.81 |
| 25 | 30.67 | 27.53 | 29.81 | 29.34 | 70.66 | 1.62 |
| 12.5 | 38.39 | 36.22 | 35.16 | 36.59 | 63.41 | 1.65 |
| 6.25 | 69.12 | 67.54 | 62.95 | 66.54 | 33.46 | 3.21 |
| 3.125 | 84.27 | 86.13 | 80.56 | 83.65 | 16.35 | 2.84 |

Example 9

Cytotoxic Testing of A549 Cell Line (Lung Cancer)

Figure 9:
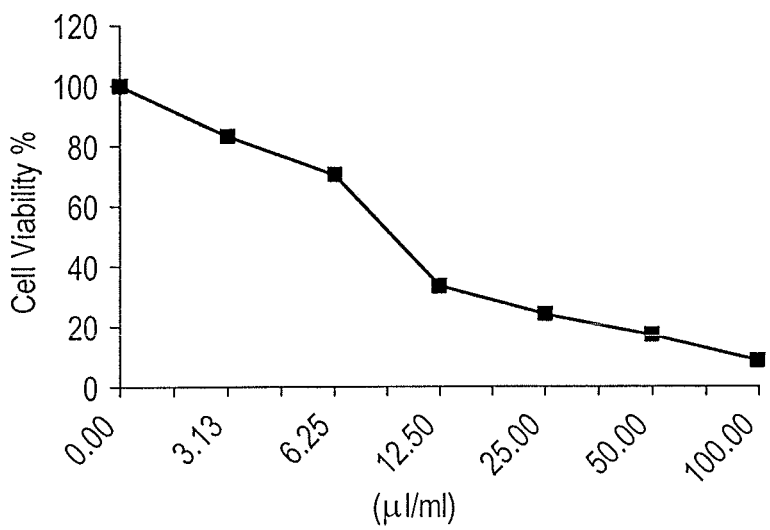
FIG. 9 is a plot of the cell viability (%) of the A549 cell line as a function of the concentration (μl/ml) of synthesized ursolic acid nanoparticles.

The cytotoxic activity of the ursolic acid nanoparticles against the A549 cell line (Human lung adecarcinoma epithelial cell line) was tested as described in the procedure of Example 5. The results are shown graphically in FIG. 9. The data shown graphically in FIG. 9 are summarized in Table 4 as follows.

TABLE 4

Inhibitory activity of ursolic acid nanoparticles against A549 cells, $IC_{50} = 9.7$

| Sample conc. (µl/ml) | % Viability (3 Replications) | | | | % Inhibition | Standard Deviation (±) |
|---|---|---|---|---|---|---|
| | 1st | 2nd | 3rd | Mean | | |
| 100 | 10.45 | 8.72 | 7.28 | 8.82 | 91.18 | 1.59 |
| 50 | 17.39 | 19.43 | 14.75 | 17.19 | 82.81 | 2.35 |
| 25 | 25.78 | 24.26 | 22.81 | 24.28 | 75.72 | 1.49 |
| 12.5 | 36.24 | 32.96 | 30.87 | 33.36 | 66.64 | 2.71 |
| 6.25 | 74.16 | 71.32 | 65.93 | 70.47 | 29.53 | 4.18 |
| 3.125 | 83.22 | 85.19 | 81.42 | 83.28 | 16.72 | 1.89 |

Example 10

Cytotoxic Testing of Hela Cells (Cervical Cancer)

Figure 10:
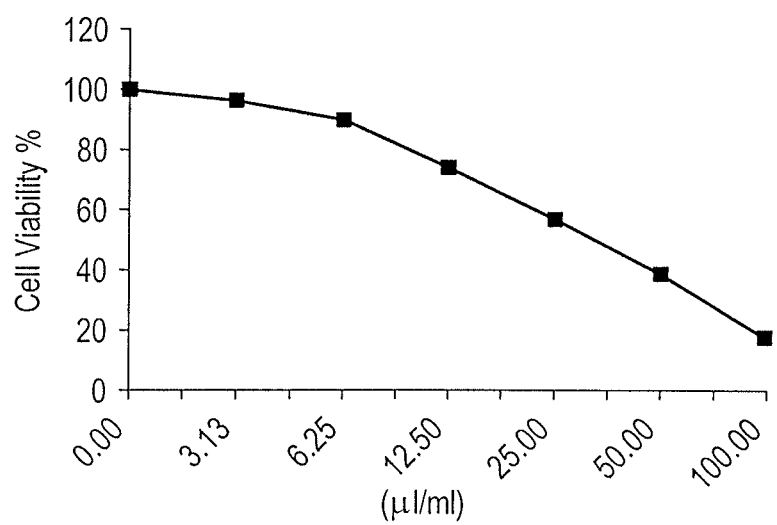
FIG. 10 is a plot of the cell viability (%) of the Hela cell line as a function of the concentration (μl/ml) of synthesized ursolic acid nanoparticles.

The cytotoxic activity of the ursolic acid nanoparticles against the Hela cell line (Human cervical cancer cell line) was tested as described in the procedure of Example 5. The results are shown graphically in FIG. 10. The data shown graphically in FIG. 10 are summarized in Table 5 as follows.

TABLE 5

Inhibitory activity of ursolic acid nanoparticles against Hela cells, $IC_{50} = 34.7$

| Sample conc. (µl/ml) | % Viability (3 Replications) | | | | % Inhibition | Standard Deviation (±) |
|---|---|---|---|---|---|---|
| | 1st | 2nd | 3rd | Mean | | |
| 100 | 17.36 | 20.82 | 14.95 | 17.71 | 82.29 | 2.95 |
| 50 | 38.91 | 41.06 | 36.88 | 38.95 | 61.05 | 2.09 |
| 25 | 53.27 | 56.89 | 60.73 | 56.96 | 43.04 | 3.73 |
| 12.5 | 71.65 | 78.18 | 72.39 | 74.07 | 25.93 | 3.58 |
| 6.25 | 89.54 | 91.32 | 89.12 | 89.99 | 10.01 | 1.17 |
| 3.125 | 98.32 | 94.06 | 96.24 | 96.21 | 3.79 | 2.13 |

It will be noted that Al-Massarani et al., "New Cytotoxic Seco-Type Triterpene and Labdane-Type Dipertenes from *Nuxia oppositifolia*", Molecules, Vol. 22, Iss. 3, 389 (March 2017) reported the isolation of ursolic acid from *N. oppositifolia* by a similar process of ethanol extraction followed by chromatographic separation with an n-hexane-ethyl acetate gradient, but without further processing to convert the isolated compound to nanoparticles. Massarani et al. further reported that cytotoxic testing of the isolated compound (compound 10) produced $IC_{50}$ values of 50.2 µg/ml against Hela cells, 65.2 µg/ml against A549 cells, and 47.76 µg/ml against MDA (breast cancer cells, as compared to the 34.7, 9.7, and 18.5 (against MCF-7 breast cancer cells) µg/ml values reported above for the synthesized ursolic acid nanoparticles. The present inventors believe that the lower $IC_{50}$ values obtained for nanoparticles of ursolic acid are unexpected and demonstrate that ursolic acid nanoparticles have greater cytotoxic activity against cancer cells than the originally isolated compound as it exists in nature.

Example 11

Antimicrobial Activity

Antimicrobial tests were carried out by agar well diffusion according to the National Committee for Clinical Laboratory Standards (NCCLS) criteria.

Bacterial and fungal suspensions were prepared at 0.5 McFarland standard turbulence in a volume of 100 μL and were cultivated on Mueller-Hinton agar and Sabouraud dextrose media punched with 6-mm diameter wells for the bacteria and fungi, respectively. Then, 100 μl of 10% tested sample was added to the wells, while 10% DMSO was used as the negative control. Ampicillin, gentamicin, and amphotericin B (30 μg/mL) were used as standard agents against the Gram-positive bacteria, Gram-negative bacteria, and fungi, respectively. After incubation of the plates at 37° C. for 18 to 24 h, the antimicrobial activity was evaluated by measuring the diameter of the inhibition zones. Each test was performed in triplicate and the average of the results was calculated. The extraction solvents were used as negative controls (NCCLS, 2002; 2004). The results are shown in Table 6, below.

TABLE 6

Antimicrobial activity of ursolic acid nanoparticles

| Microorganisms | Samples | |
|---|---|---|
| | Ursolic Acid Nanoparticles | Reference Drug |
| Fungi | | Amphotericin B |
| *Absidia corymbifera* (RCMB 02564) | 18.3 ± 0.14 | 23.0 ± 0.10 |
| *Geotricum candidum* (RCMB 05007) | 18.6 ± 0.11 | 27.0 ± 0.20 |
| *Candida albicans* (RCMB) | 17.3 ± 0.28 | 25.7 ± 0.10 |
| Gram Positive Bacteria: | | Ampicillin |
| *Staphylococcus aureus* (RCMB 010027) | 21.3 ± 0.19 | 27.3 ± 0.14 |
| *Staphylococcus epidermidis* (RCMB 010024) | 21.6 ± 0.54 | 25.0 ± 0.18 |
| *Streptococcus pyogenes* (RCMB 010015) | 21.3 ± 0.24 | 26.3 ± 0.34 |
| Gram Negative Bacteria: | | Gentamycin |
| *Proteous vulgaris* (RCMB 010085) | 20.6 ± 0.10 | 23.4 ± 0.30 |

TABLE 6-continued

Antimicrobial activity of ursolic acid nanoparticles

| Microorganisms | Samples | |
|---|---|---|
| | Ursolic Acid Nanoparticles | Reference Drug |
| *Klebsiella pneumoniae* (RCMB 0010093) | 18 ± 0.14 | 26.4 ± 0.15 |
| *Salmonella enteritidis* (RCMB 010084) | 22.3 ± 0.27 | 25.2 ± 0.18 |

Values are Zone of Inhibition (±S.D.)
Well diameter: 6 mm
Sample tested: 100 μl using diffusion agar technique It is to be understood that the synthesis of ursolic acid nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of inhibiting propagation of cancer cells, comprising the steps of:
   determining that the cancer cells are from the group consisting of MCF-7 (Breast carcinoma) cells, HepG-2 (Hepatocellular carcinoma) cells, HCT-116 (Colon carcinoma) cells, A549 (Lung cancer) cells, and Hela (cervical cancer) cells; and
   administering an effective amount of ursolic acid nanoparticles into contact with the cancer cells, wherein the ursolic acid nanoparticles are made by the method comprising the steps of:
   (a) dissolving ursolic acid powder in methanol, wherein the ursolic acid powder is from the aerial parts of *Nuxia oppositifolia*;
   (b) boiling water for five minutes;
   (c) adding the ursolic acid dissolved in methanol dropwise at a flow rate of 0.1-0.3 ml/min to the boiled water dropwise under ultrasonic conditions to produce an aqueous ursolic acid solution;
   (d) sonicating the ursolic acid of step (c) for 20 minutes;
   (e) stirring the sonicated solution of step (d) for about 15 minutes; and
   (f) drying the solution of step (e) to obtain the ursolic acid nanoparticles, wherein the dried ursolic acid nanoparticles have a particle size between 10 nm and 100 nm.

* * * * *